United States Patent [19]
Shah

[11] Patent Number: 6,081,737
[45] Date of Patent: *Jun. 27, 2000

[54] APPARATUS FOR VASCULAR MAPPING AND METHODS OF USE

[76] Inventor: Ajit Shah, 112 Crescent Ave., Portola Valley, Calif. 94028

[ * ] Notice: This patent is subject to a terminal disclaimer.

[21] Appl. No.: 09/132,561

[22] Filed: Aug. 11, 1998

Related U.S. Application Data

[63] Continuation-in-part of application No. 08/828,317, Mar. 28, 1997, Pat. No. 5,833,605.

[51] Int. Cl.[7] .......................................................... A61B 5/04
[52] U.S. Cl. .......................... 600/393; 600/114; 600/117; 33/512
[58] Field of Search ..................................... 600/114, 117, 600/118, 585, 393; 33/511, 512, 542–544, 544.2, 544.5, 544.6, 542.1, 544.3; 606/280

[56] References Cited

U.S. PATENT DOCUMENTS

| | | | |
|---|---|---|---|
| 2,712,697 | 3/1955 | Lebourg | 33/544.3 |
| 3,755,908 | 9/1973 | Vernooy | 33/542 |
| 4,235,020 | 11/1980 | Davis et al. | 33/544 |
| 4,299,033 | 11/1981 | Kinley et al. | 33/542 |
| 4,301,677 | 11/1981 | Fisher | 33/542 |
| 4,493,153 | 1/1985 | Esken | 33/542 |
| 4,813,930 | 3/1989 | Elliott . | |
| 4,878,893 | 11/1989 | Chin | 600/127 |
| 5,005,559 | 4/1991 | Blanco et al. | 600/117 |
| 5,239,982 | 8/1993 | Trauthen | 600/117 |
| 5,396,880 | 3/1995 | Kagan et al. | 660/117 |
| 5,415,166 | 5/1995 | Imran . | |
| 5,575,754 | 11/1996 | Konomura | 600/117 |
| 5,586,968 | 12/1996 | Grundl et al. | 600/114 |
| 5,665,052 | 9/1997 | Bullard | 600/114 |

*Primary Examiner*—John P. Leubecker
*Attorney, Agent, or Firm*—Fish & Neave; Nicola A. Pisano

[57] ABSTRACT

Apparatus and methods are provided for mapping an interior surface of a section of a body lumen comprising a catheter having a plurality of elements circumferentially disposed around its distal end that contact the interior surface of a body lumen and provide output signals corresponding to the local diameter of the lumen. In a preferred embodiment, the contacts are of an electrical-mechanical type, such that an output signal may be generated which is proportional to the degree of deflection of the contact caused by the local diameter of the body lumen. The distal end of the catheter is translated through the body lumen for a predetermined distance, while the output signals are reproduced on either an analog recorder or as a digital three-dimensional display. A drive system for translating the catheter, and methods of use, are also provided.

19 Claims, 5 Drawing Sheets

APPARATUS FOR VASCULAR MAPPING AND METHODS OF USE

REFERENCE TO RELATED APPLICATIONS

This application is a continuation-in-part of U.S. patent application Ser. No. 08/828,317 filed Mar. 28, 1997, now U.S. Pat. No. 5,833,605.

FIELD OF THE INVENTION

The present invention relates to apparatus and methods for mapping the interior surface topology of a body lumen, for example, preparatory to or after performing a dilatation procedure, such as percutaneous transluminal angioplasty ("PTA"). More particularly, the apparatus and methods of the present invention provide a simple and relatively uncomplicated system by which the diameter of a body lumen may be characterized.

BACKGROUND OF THE INVENTION

In recent years minimally-invasive apparatus and methods for treating narrowing of body vessels, especially the coronary arteries, have been developed as a substitute for invasive surgical procedures, such as bypass grafting. For example, percutaneous transluminal coronary angioplasty ("PTCA") is commonly performed on patients to restore patency to coronary arteries that have become narrowed due to vascular disease and plaque buildup.

Typically, PTCA procedures involve the insertion of a mechanical dilatation device—usually a balloon catheter—transluminally to a constricted location of a coronary artery. The device is then dilated to a selected diameter, and the pressure maintained approximately constant to compress plaque lining the artery, thereby increasing the diameter of the artery and restoring flow therethrough.

A drawback common to PTCA, and dilatation procedures that are performed in other body lumens, is the inability to gauge the diameter of the body lumen. Such information is important for assessing the potential efficacy of a proposed course of therapy, for example, PTCA, PTCA followed by the implantation of a vascular prosthesis, or coronary artery bypass grafting ("CABG"). Often, due to the tortuosity of a vessel, it is difficult to assess the degree of narrowing of the vessel using conventional fluoroscopic and angiographic techniques. In particular, fluoroscopy provides only a two-dimensional view of the vessel, and may not adequately represent the degree of constriction occurring in three dimensions.

One promising method that has been developed to assess the topology of diseased vessels is intraluminal ultrasound technology. Typically, a catheter carrying an ultrasound element is disposed within a diseased vessel to provide a cross-sectional view of the vessel wall (and stenosis) at a given longitudinal location within the vessel. Drawbacks of intraluminal ultrasound systems, however, are that the images are typically fairly noisy, and of such high contrast that they have limited utility. Moreover, because the ultrasound image is in a plane transverse to the vessel axis, it is difficult to obtain an accurate mapping of the vessel along the entire section of the stenotic region. While attempts to construct three-dimensional views of the vessel and stenotic region using offline postprocessing have been made, such systems are expensive, require specialized hardware, and are time consuming, leading to limited acceptance in the medical community.

In view of the foregoing, it would be desirable to provide apparatus and methods for providing, in real-time, a detailed map of the interior surface topology of a vessel, including a stenotic region.

It also would be desirable to provide apparatus and methods for mapping the interior surface topology of a body lumen that employs relatively simple electrical and mechanical components, thereby providing a system that costs less than previously known ultrasound technology, but which provides significantly better performance.

It further would be desirable to provide apparatus and methods for providing, in near real-time, a three-dimensional view of the interior surface of a vessel, using low cost, readily available components.

SUMMARY OF THE INVENTION

In view of the foregoing, it is an object of this invention to provide apparatus and methods for providing, in real-time, a detailed map of the interior surface topology of a vessel, including a stenotic region.

It is another object of the present invention to provide apparatus and methods for mapping the interior surface topology of a body lumen that employs relatively simple electrical and mechanical components, thereby providing a system that costs less than previously known ultrasound technology, but with significantly better performance.

It is a further object of the invention to provide apparatus and methods for providing, in near real-time, a three-dimensional view of the interior surface of a vessel, using low cost, readily available components.

These and other objects of the present invention are accomplished by providing a catheter having a plurality of simple mechanical elements circumferentially disposed on a distal end of the catheter. The elements contact the interior surface of a body lumen and provide output signals corresponding to the local diameter of the lumen. The distal end of the catheter may be translated through the body lumen for a predetermined distance, while the output signals are reproduced on either an analog or digital display.

In a preferred embodiment of the present invention, the apparatus comprises a catheter having a plurality of contacts disposed around its circumference. The contacts are of an electrical-mechanical type, such that an output signal may be generated which is proportional to a degree of deflection of the contact caused by the local diameter of the body lumen. The catheter may be translated manually or by a drive system and includes an encoder that outputs a signal corresponding to an instantaneous position of the distal end of the catheter.

Outputs generated by the contacts may be amplified, converted to deflection values using suitable logic (e.g., a look-up table), and provided to an analog recorder, for example, a strip chart having one channel per contact. Alternatively, a digital to analog converter may be used to sample the output signals of the contacts. The digitized samples may then be transmitted to a digital computer for some simplified post-processing and displayed on a video terminal as a three-dimensional image.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention relates generally to apparatus and methods for mapping the interior structures of a body lumen, especially a vessel including a congenital constriction or stenosis. In accordance with the present invention, a catheter is provided that includes a plurality of contacts that measure the diameter of a body lumen. The present invention is particularly useful for mapping and characterizing the topology of a vessel, for example, prior to treatment, to determine an appropriate course of treatment. The apparatus of the present invention also may be advantageously used after a minimally-invasive procedure, such as PTCA, has been completed, to assess the efficacy of the treatment.

Figure 1:
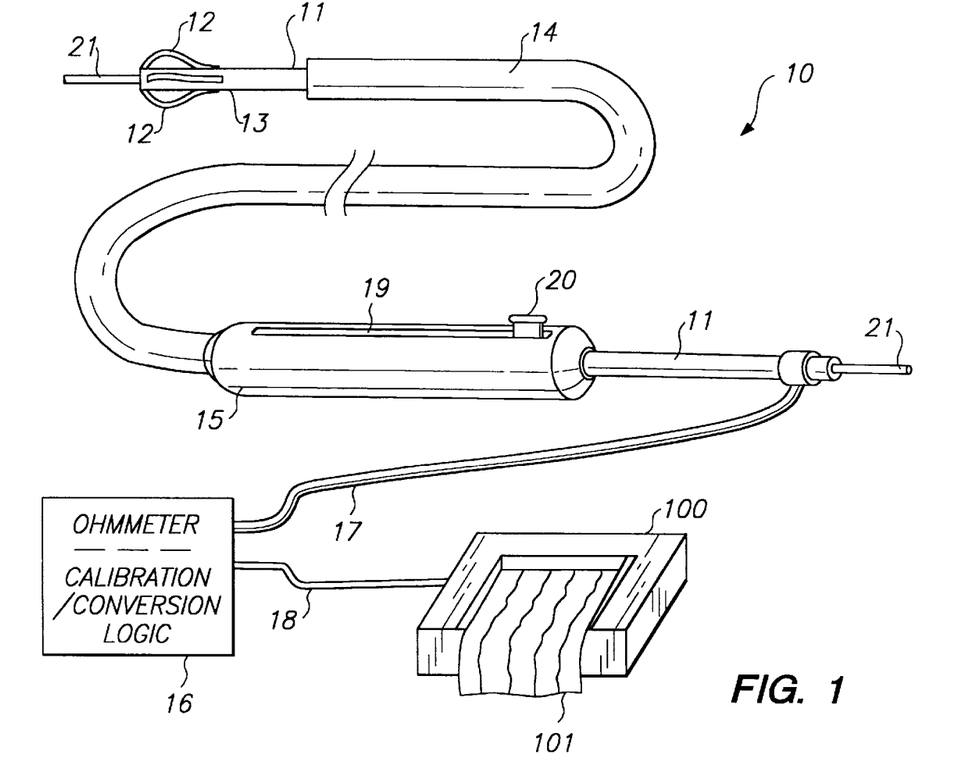
FIG. 1 is a perspective view (not to scale) of an illustrative embodiment of apparatus constructed in accordance with the present invention.

Referring to FIG. 1, illustrative apparatus 10 constructed in accordance with the present invention is described. Apparatus 10 (which is not drawn to scale) includes catheter 11 having plurality of contacts 12 disposed on distal end 13, outer sheath 14, and handle portion 15. Measurement and processing circuitry 16 is connected to contacts 12 via cable 17 and conductive leads disposed in catheter 11. Measurement and processing circuitry 16 illustratively includes ohmmeter circuitry that senses the resistance of contacts 12 corresponding to the degree of radial deflection caused by a constriction within the body lumen, as described in greater detail hereinafter. The output of measurement and processing circuitry 16 is provided via cable 18 to analog chart recorder 100. Handle portion 15 includes slot 19 through which button 20 extends for translating catheter 11 within handle 15. Apparatus 10 is preferably inserted transluminally to the site of a diseased vessel by advancing apparatus 10 along guide wire 21, using, for example, an over-the-wire arrangement. Analog recorder 100 preferably provides strip chart 101 that records the output signal generated by each one of the plurality of contacts 12.

Figure 2:
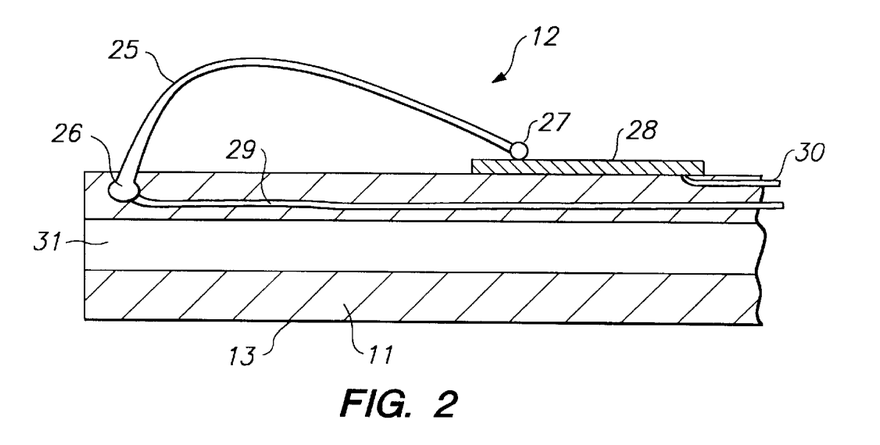
FIG. 2 is a cross-sectional view of a single contact employed in the apparatus of FIG. 1.
Figure 3A:
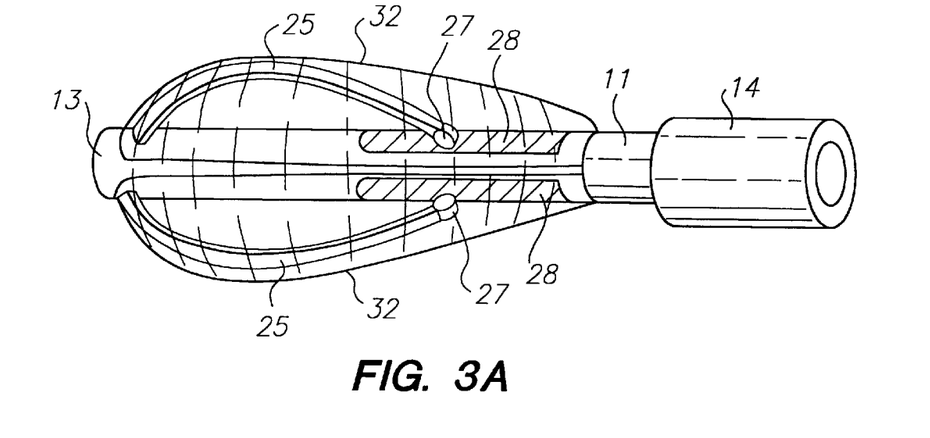
FIGS. 3A and 3B are, respectively, a partial perspective view and an end view of the distal end of the apparatus of FIG. 1.
Figure 3B:
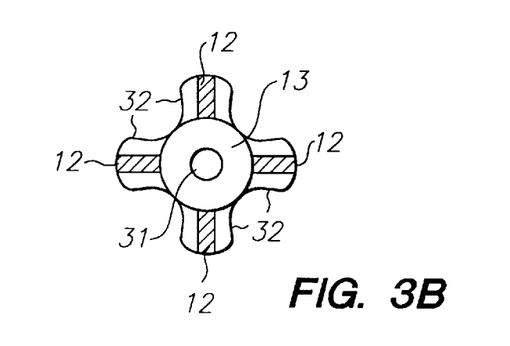

Referring now to FIGS. 2, 3A and 3B, distal end 13 of catheter 11 includes plurality of contacts 12 which are sensed by the ohmmeter circuitry of measurement and processing circuitry 16 to generate a signal proportional to the degree of radial deflection of the contacts caused by the topology of the inner wall of the body lumen. In FIG. 2, a single contact is depicted as bow-type spring 25 having distal end 26 embedded in distal end 13 of catheter 11, and bulbous proximal end 27 that slides along resistive strip 28. Distal end 26 of bow-type spring 25 is connected by conductive lead 29 to cable 17 and the ohmmeter circuitry. Resistive strip 28 likewise is connected by conductive lead 30 and cable 17. Conductive leads 29 and 30 are illustratively shown in FIG. 2 embedded in catheter 11; alternatively, a lumen (separate from guide wire lumen 31) may be provided for housing the conductive leads.

Alternatively, the position of bow-type spring 25 may be reversed with respect to catheter shaft 11, i.e., affixed to catheter 11 at a proximal position with bulbous distal end arranged to slide in a distal direction when the bow-type spring is deflected inward. It will be understood by one of skill in the art that the following description of the present invention applies equally to such alternative embodiments.

As shown in FIG. 3A (in which only two contacts 12 are illustrated for clarity), bow-type springs 25 preferably have a rectangular cross-section, to prevent sideways tilting of proximal end 27. In accordance with the present invention, resistive strip 28 has a predetermined resistance per unit length. When bulbous proximal end 27 of bow-type spring 25 contacts resistive strip 28, it forms an electrical circuit (which includes the ohmmeter circuitry of measurement and processing circuitry 16). As is conventional, the ohmmeter circuitry includes circuitry for passing a very low current through the contact circuit to determine the overall resistance of the contact circuit. The ohmmeter circuitry preferably employs a very low voltage DC power supply, for example, a 9 volt DC battery, to individually measure the resistance of each of contacts 12.

The electrical resistance presented by resistive strip 28 varies linearly with the distance between proximal end 27 of bow-type spring 25 and the point of connection of wire 30 to resistive strip 28. Thus, as bow-type spring 25 deflects radially from its unloaded position, proximal end 27 slides proximally along resistive strip 28, reducing the resistance of the circuit. The electrical resistance of bow-type spring 25 and resistive strip 28, as sensed by the ohmmeter circuitry, accordingly may be calibrated to the amount of radial deflection of bow-type spring 25.

Measurement and processing circuitry 16 also comprises calibration logic for storing values obtained during calibration, and conversion logic for converting measured values of resistance to radial deflections. In particular, calibration and conversion logic comprise circuitry for correlating a measured value of resistance to radial deflection by comparing the measured value to a stored calibration table containing radial deflections as a function of resistance (for each contact). The circuitry may then interpolate within the table to compute a radial deflection corresponding to the measured resistance. Of course, other types of conversion logic may be used. For example, an empirical equation may be fit to the calibration data of deflection versus resistance, and the resulting empirical equation may be programmed into the calibration and conversion logic, instead of the look-up table described hereinabove.

As shown in FIG. 3B, in a preferred embodiment, apparatus 10 includes four contacts 12, as described hereinabove, spaced equi-distant apart around the circumference of catheter 11. To electrically isolate contacts 12 from fluids flowing in the body lumen, as well as to prevent conductive fluids from providing erroneous resistance measurements, each of contacts 12 is enclosed within a loose-fitting light-weight plastic covering 32. The plastic covering, which may be formed, for example, from thin polyethylene, forms a series of lobes over each of contacts 12. While plastic covering 32 provides a fluid impervious barrier and electrical isolation between contacts 12 and body fluids, the plastic covering is sufficiently thin that it does not interfere with radial deflection of contacts 12.

Figure 4:
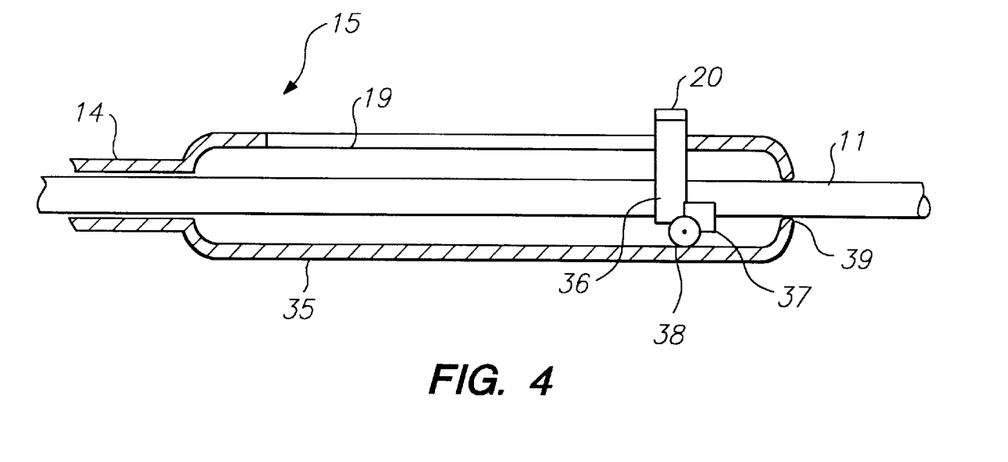
FIG. 4 is a cross-sectional view of the handle portion of the apparatus of FIG. 1.

Referring now to FIG. 4, handle portion 15 of apparatus 10 is described in greater detail. Handle portion 15 comprises an enlarged portion 35 that forms a hand grip to which the proximal end of outer sheath 14 is affixed. Handle portion 15 includes longitudinal slot 19. Arm 36 is affixed to catheter 11 and includes a portion extending through slot 19 and terminating in button 20. Arm 36 carries encoder 37 and traction wheel 38 on its lower end. Traction wheel 38 engages the inner surface of enlarged portion 35, so that it rotates as arm 36 is translated in slot 19. Encoder 37 is employs a modified form of a rotary encoder typically used in computer pointing devices (i.e., a mouse), so that traction wheel causes encoder 37 to generate pulses corresponding to longitudinal displacement of arm 36. Encoder 37 is coupled to display device 100 via suitable lead wires (not shown).

Catheter 11 is slidably disposed in outer sheath 14 so that when button 20 is moved in the distal direction, distal end 13 of catheter 11 is translated an equal distance. Accordingly, catheter 11 extends through hole 39 in the proximal end of handle portion 15 at least a distance equal to the length of slot 19 (with cable 17 connected to catheter 11 proximally of that length). Consequently, the distal end of catheter 11 may be translated in the distal direction (beyond the end of outer sheath 14) by a distance equal to the length of slot 19. As arm 36 is translated in slot 19, encoder 37 outputs a signal corresponding to the instantaneous position of arm 36 within handle portion 15. This signal also corresponds to the displacement of distal end 13 of apparatus 10 within a vessel being mapped, and may be output by display device 100 to provide an indication of diametral change of the vessel as a function of distance, as described hereinbelow.

In a preferred embodiment of the invention, catheter 11 and outer sheath 14 comprise material typically used in catheter construction, for example, poly vinyl chloride or high density polyethylene. Catheter 11 and outer sheath 14 are preferably about 1.0 m and 1.1 m long, respectively, while outer sheath preferably has an outer diameter suitable for advancement within target body lumen. Contacts 12 preferably comprise a resilient metal alloy, such as stainless steel, while resistive strips 28 may comprise a suitable high resistance foil. Conductive leads 29 and 30 may comprise copper or a copper alloy wires, while measurement and processing circuitry 16 preferably includes four channels for measuring the resistance across each of contacts 12 individually. Alternatively, measurement and processing circuitry 16 may include multiplexing logic for measuring the resistances of contacts 12 serially. The measured resistances of contacts 12 are then converted to appropriate values of radial deflection, for example, using a suitable analog or digital look-up table, and the resulting deflection values are provided to analog recorder 100.

Figure 5A:
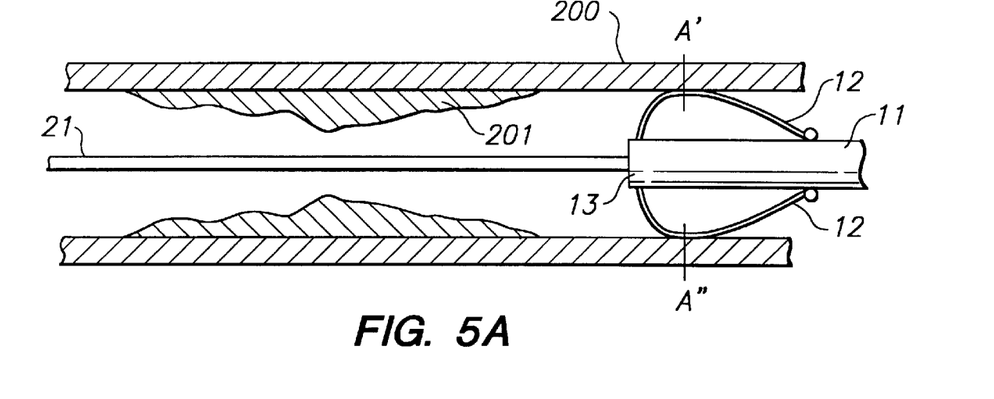
FIGS. 5A and 5B are cross-sectional views showing the deflection of the contacts of the apparatus of FIG. 1 as it is advanced through a section of a body lumen.
Figure 5B:
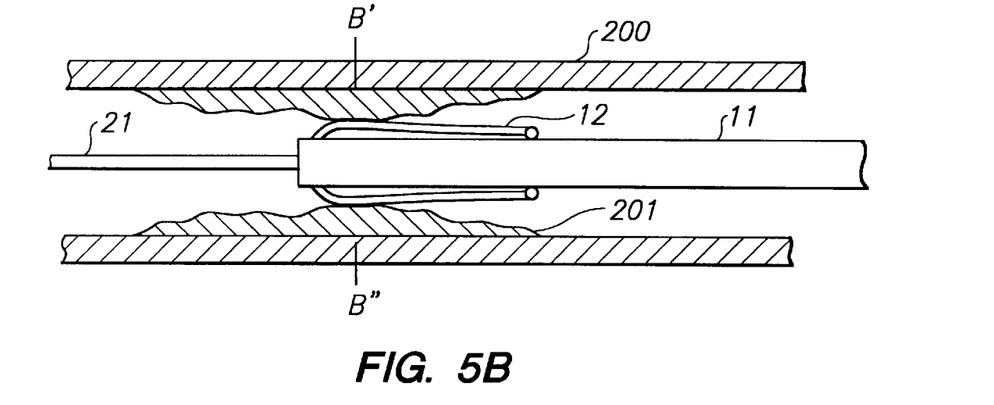
Figure 6:
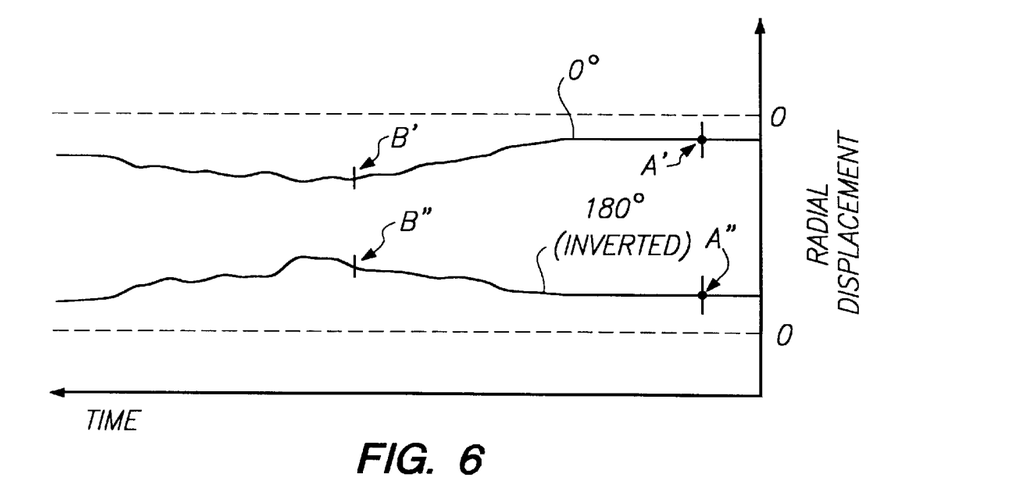
FIG. 6 is a portion of a strip chart generated by advancing the apparatus of FIG. 1 through the body lumen depicted in FIG. 5.

With respect to FIGS. 5A, 5B and 6, operation of the apparatus of the present invention is now described. In FIG. 5A, distal end 13 of apparatus 10 is shown disposed on guide wire 21 that spans a diseased section 201 of body lumen 200. When positioned as shown in FIG. 5A, contacts 12 have deflections A' and A", corresponding to the healthy portion of the body lumen, and button 20 on handle portion 15 is in the proximal-most position. The clinician then slowly slides button 20 in the distal direction with one hand while holding handle portion immobile with the other hand, thereby causing distal end 13 to traverse diseased section 201 of body lumen 200. Alternatively, apparatus 10 may be employed by first moving arm 36, and distal end 13, to the distal-most position, and then retracting arm and distal end 13 in a proximal direction to measure the vessel topology as a function of distance.

As seen in FIG. 5B, as catheter 11 is translated in vessel 200, contacts 12 are deflected inward by amounts B' and B" by the constriction in section 201. Accordingly, measurement and processing circuitry 16 senses the reduction in resistance in the individual contacts, and computes a corresponding value of radial deflection.

The output of apparatus 10 is then transmitted to analog recorder 100, which provides a visual indication of the topology of section 201 as illustrated in FIG. 6. In FIG. 6, traces of the deflections from the 0 degree contact position and the 180 degree position are plotted side by side (with the 180 degree signal inverted), thereby providing a visual representation of the narrowing within the vessel (the traces from the other pair of contacts may be likewise reproduced with one signal inverted). Output of encoder 37 of handle portion 15 may also be displayed on display device 100, so that the narrowing of the vessel as a function of distance along the length of the vessel may be observed. The clinician may then retract button 20 and repeat movement of catheter 11 to determine, in real-time, the local diameter of the diseased section of body lumen at a given location within the vessel.

Figure 7:
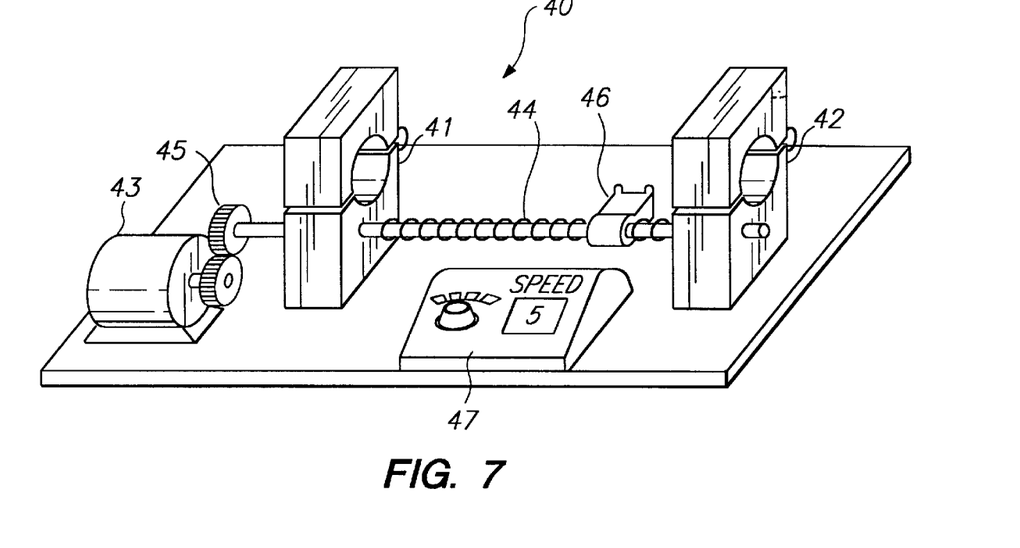
FIG. 7 is a perspective view of a motorized drive system for use with the handle portion of FIG. 4.

Referring now to FIG. 7, drive system 40 is described for use with the apparatus of FIG. 1 for automatically generating a three-dimensional map of the internal structure of a body lumen. Drive system 40 includes support members 41 and 42 for accepting handle portion 15 of apparatus 10, motor 43, spiral gear 44 coupled to the output shaft of motor 43 via pinion gear 45, button cradle 46, and motor controller 47. Handle portion 15 of apparatus 10 is fastened into support blocks 41 and 42 so that button 20 is engaged in button cradle 46. When motor 43 is activated by motor controller 47, it rotates, causing spiral gear 44 to rotate at a user selected speed. Rotation of spiral gear 44 in turn translates button cradle 46, which causes button 20 on handle 15 to be moved at a uniform speed. Drive system 40 may be advantageously used to translate distal end 13 of catheter 11 in accordance with the method described above.

Figure 8:
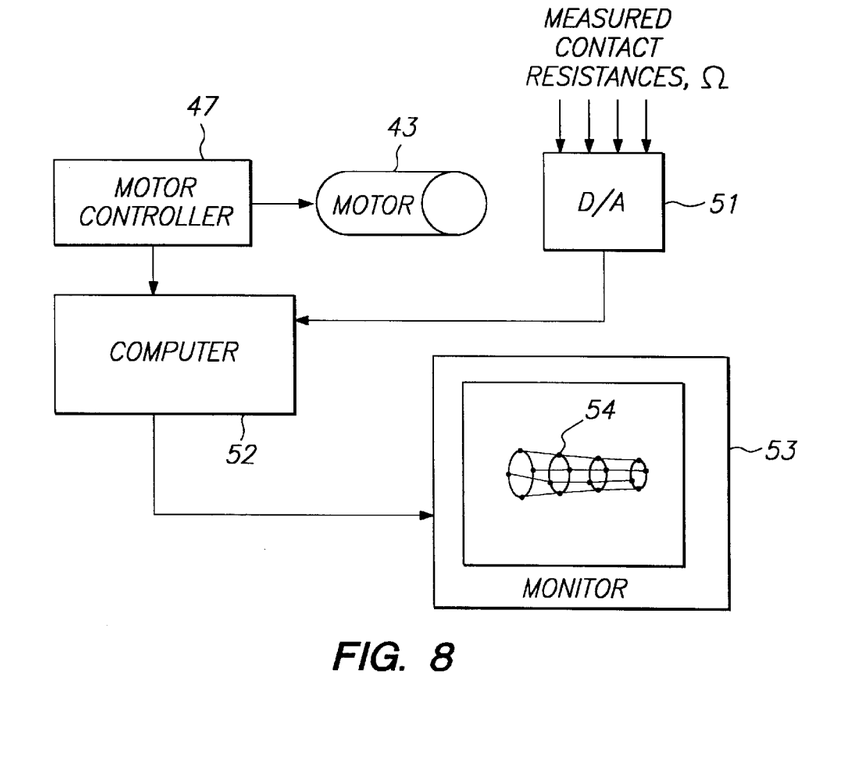
FIG. 8 is a block diagram of the components needed to render a digital three-dimensional view of interior surface of a body lumen employing the apparatus of FIG. 1.

Referring now to FIG. 8, system 50 is described in which apparatus 10 and drive system 40 may be used to generated a three-dimensional image of the topology of the body lumen. System 50 includes drive system 40 of FIG. 7, including motor controller 47 and motor 43, digital sampler 51, general purpose computer 52 and video monitor 53. Digital sampler samples the measured resistances from contacts 12, and provides that information to computer 52.

Computer 52, which may be, for example, an IBM-compatible personal computer, is programmed to correlate the position data output by encoder 37 with the digitized samples of the measured resistance, and to compute the radial deflections from the measured resistances (based on the calibration data or an empirically derived formula). Computer 52 then computes a three dimensional image of the interior of the body lumen using well known programming techniques for rendering three-dimensional views from arrays of data. Video monitor 53 therefore provides a near real-time three-dimensional map of the topology of the diseased section of the body lumen, shown as illustrative display 54 on video monitor 53.

As will be apparent from the foregoing description, the present invention provides apparatus and methods for obtaining real-time visual displays, i.e., either as two-dimensional analog graphs as a function of distance, or three-dimensional digital images, of the interior surface topology of a body lumen, using simple electrical and mechanical components, and readily available processing hardware.

The embodiment described hereinabove illustratively includes four contacts 12 spaced equidistant around the circumference of the catheter, although as few as two and more than four contacts may be used as required for a particular application. Advantageously, when three or more contacts 12 are used to characterize the body lumen, it is irrelevant whether the guide wire is disposed concentrically within the body lumen. For example, if the guide wire is off-center in a three contact system, then two of the contacts will measure higher deflections, while the third contact will measure correspondingly smaller deflections. In the aggregate, however, the local diameter of the body lumen should nevertheless be accurately determined.

Figure 9A:
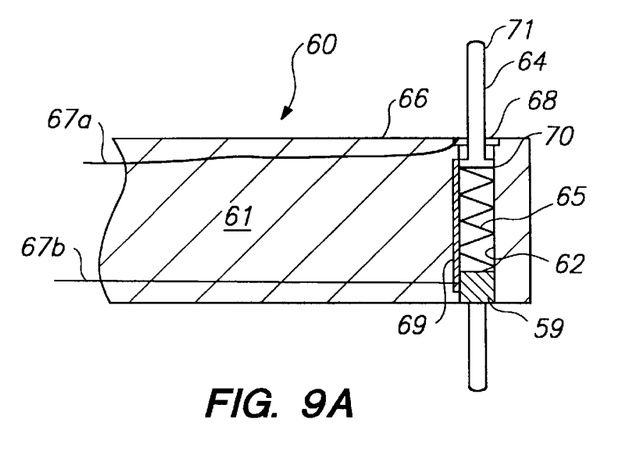
FIGS. 9A and 9B are, respectively, side and end sectional views of an alternative contact for use in apparatus constructed in accordance with the present invention.
Figure 9B:
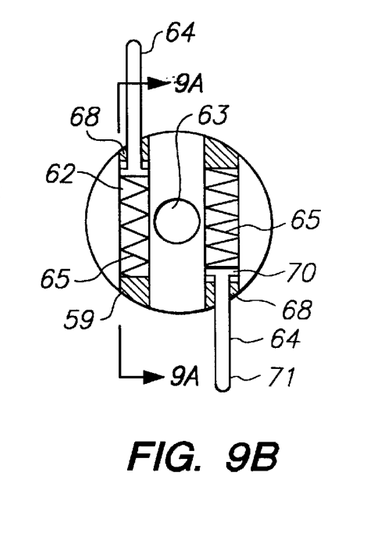

Referring now to FIGS. 9A and 9B, an alternative embodiment of apparatus 60 of the present invention is described. Apparatus 60 resembles the device of FIG. 1 except that the bow-type sensors of apparatus 10 of FIG. 1 have been replaced with a resistive plunger arrangement. In particular, catheter 61 includes bores 62 that extend along chords of the cross-section of the catheter on either side of central guidewire lumen 63. Plungers 64 are biased by springs 65 to project from the surface of catheter 66, while springs 65 are retained in bore 62 by endcaps 59. Plungers 64 also may include roller-type contacts (not shown) on their distal ends 71 for contacting the interior of the body lumen.

Electrical lead 67a connects to conductive collar 68, which is in sliding electrical contact with plunger 64. Collar 67 both energizes plunger 64 and retains the plunger within bore 62. Electrical lead 67b is coupled to film resistor 69 disposed on an interior surface of bore 62. Film resistor has a uniform resistance per unit length, and is in electrical contact with flanged edge 70 of plunger 64.

Plunger 64 forms part of a circuit including electrical lead 67a, collar 68, plunger 64, flange 71, film resistor 69 and electrical lead 67b. When plunger 64 is displaced inwardly due to a constriction within the body lumen contacting tip 71 of plunger 64, the depth of depression of the plunger creates a corresponding change in the overall resistance of the circuit. This change in resistance is detected by circuitry similar to that described hereinabove with respect to FIGS. 1–3.

Figure 10:
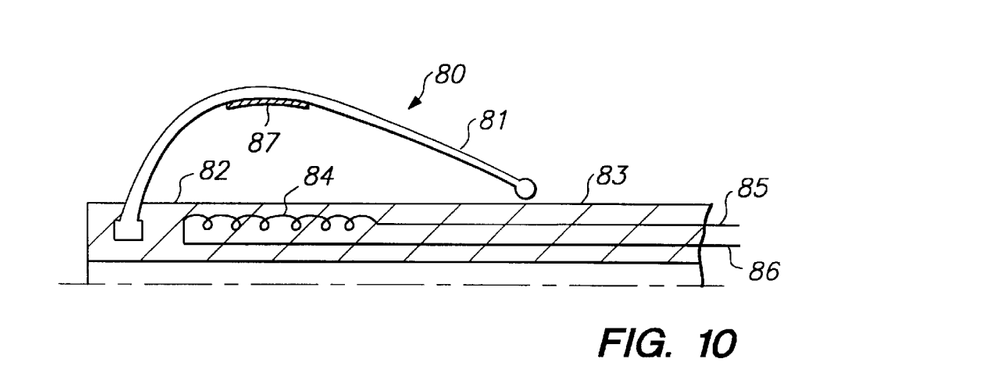
FIG. 10 is a partial side sectional view of an alternative embodiment of the present invention wherein deflection is detected based upon inductive techniques.

With respect to FIG. 10, another alternative embodiment of the apparatus of the present invention is described. Only the distal end of apparatus 80 is shown in detail, with the remainder of the apparatus being similar in appearance to the device of FIG. 1. Apparatus 80 includes bow-type spring 81 which is mounted in a distal end 82 of catheter 83. Catheter 83 includes inductive coil 84 embedded in its distal end region which is electrically coupled via electrical leads 85 and 86 to form part of an oscillator circuit (not shown). A magnetic material or ferrous alloy 87 is disposed on an interior face of bow spring 81 to face inductive coil 84.

Inductive coil 84 is arranged so that changes in inductance caused by movement of the magnetic material or ferrous alloy 87 in proximity to inductive coil 84 causes a frequency change in the circuit, which is then detected. Such circuitry is conventional in the design of metal detector circuits used for treasure hunting, as described, for example, in Encyclopedia of Electronic Circuits, Vols. 1–6 (edited by Rudolf Graf and William Sheets), McGraw-Hill (1996) and its extension to the present invention will be apparent to one of skill in the art of analog circuit design. The detected change in inductance caused by inward deflection of bow-spring 81 may be correlated to the deflection of the bow spring, from which the actual inward deflection of the bow spring, and hence the local diameter of the body lumen, may be computed.

Figure 11:
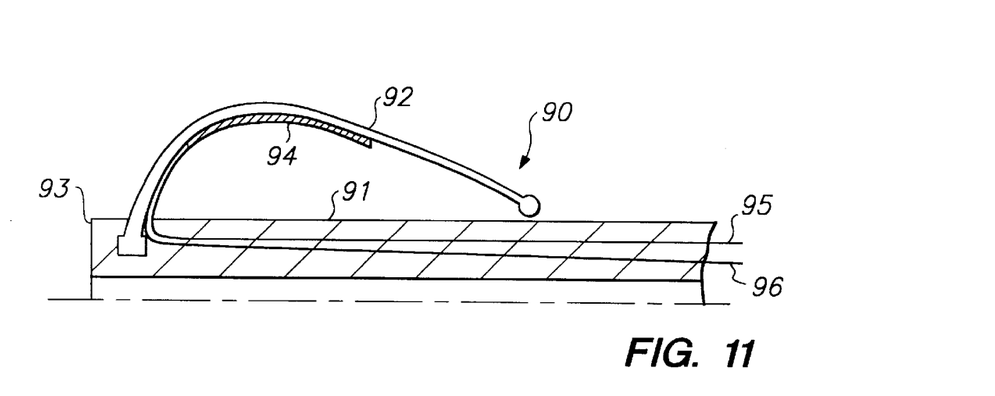
FIG. 11 is a partial side sectional view of an alternative embodiment of the present invention wherein deflection is detected using a strain gauge.

In FIG. 11 yet another alternative embodiment of apparatus constructed in accordance with the present invention is described. In FIG. 10, apparatus 90 includes catheter 91 including bow-type spring 92 affixed to its distal end 93, and strain gauge 94 affixed to bow spring 92. Strain gauge 94, which may be of the thin film type, has a resistance which varies as a function of strain induced in the gauge, and is coupled via leads 95 and 96 to measurement circuitry which is per se known. Electrical leads 95 and 96 may be embedded within catheter 91 or alternatively routed along an external surface.

As will be apparent from inspection of the embodiment of FIG. 11, deflection of bow spring 92 will impose a strain on strain gauge 94. The output of strain gauge 94 may be calibrated to correspond to deflection of the bow-spring using either analog or digital tables or formulas, as described hereinabove. Accordingly, the outputs of apparatus 90 may be used to map the topology of an interior surface of a body lumen. In addition, while the embodiment of FIGS. 1–3 are expected to require a loose-fitting light-weight plastic covering (see FIG. 3), the embodiments of FIGS. 9–11 obviate the need for such encapsulation, thereby enhancing ease of manufacture.

While the preferred embodiment has been described with respect to resistance and inductive based systems, it will be apparent to one of skill in the art of medical equipment design that other physical or electrical parameters can be advantageously used to practice the present invention. For example, deflection of springs 25 could alter the capacitance of the contact. Further, for example, springs 25 of FIG. 1 may include an optical fiber while resistive strip 28 may be replaced by a linear array of photodetectors, so that as the spring experiences greater deflections, the optical fiber illuminates photodetectors which are located progressively more proximal on catheter 11.

While preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. Apparatus for mapping an interior surface of a lumen of a patient's vasculature, the apparatus adapted for connection to a display device, the apparatus comprising:

a catheter having a proximal end, a distal end, and a portion defining a guide wire lumen, the catheter configured for percutaneous, transluminal insertion in the patient's vasculature along a guide wire;

a first contact disposed on the distal end, the first contact having a feature that varies as a function of a deflection imposed on the first contact by the interior surface of the lumen;

circuitry for measuring the feature;

circuitry for correlating the measured feature to the deflection and for providing an output to the display device corresponding to the deflection.

2. The apparatus as defined in claim 1 wherein the feature varies as a function of radial deflection of the first contact.

3. The apparatus as defined in claim 1 wherein the first contact comprises a resilient member having a bow shape, a first end and a second end, the first end affixed to the catheter, the second end free to slide a distance in a direction away from the first end as a function of the deflection of the bow shape.

4. The apparatus as defined in claim 3 wherein the second end makes a sliding connection with a strip, the feature varying as a function of the distance attained by the second end.

5. The apparatus as defined in claim 4 wherein the feature is electrical resistance, and the strip has a predetermined resistance per unit length.

6. The apparatus as defined in claim 5 wherein the circuitry for measuring the feature comprises ohmmeter circuitry for measuring the resistance of the first contact.

7. The apparatus as defined in claim 3 further comprising a strain gauge mounted on the resilient member, the strain gauge generating a signal corresponding to a degree of deflection of the resilient member.

8. The apparatus as defined in claim 3 further comprising a coil disposed within the catheter and wherein the resilient member comprises a ferrous material, so that movement of the ferrous material relative to the coil generates a detectable change in the inductance of the coil.

9. The apparatus as defined in claim 1 wherein the first contact comprises a plunger and means for detecting inward movement of the plunger.

10. The apparatus as defined in claim 1 wherein the circuitry for correlating compares a value of the measured feature to a stored calibration table containing deflections as a function of value of the feature, and interpolates within the table to compute a deflection corresponding to the measured feature.

11. The apparatus as defined in claim 1, wherein the distal end of the catheter has a circumference, the apparatus further comprising second, third and fourth contacts, the first, second, third and fourth contacts disposed around the circumference of the distal end.

12. The apparatus as defined in claim 11 wherein the first, second, third and fourth contacts are spaced equidistant apart around the circumference.

13. The apparatus as defined in claim 1 further comprising means for translating the distal end of the catheter to traverse a length of the lumen and means for generating a signal corresponding to an instantaneous position of the distal end of the catheter.

14. The apparatus as defined in claim 13 wherein the means for translating further comprises means for translating the distal end through the length of the lumen at a user selected speed.

15. The apparatus as defined in claim 13, wherein the display device comprises a video monitor, the apparatus further comprising a computer programmed to receive an output from the means for generating a signal corresponding to an instantaneous position of the distal end of the catheter, the computer programmed to provide an output to the display device representing a three-dimensional image of the interior surface topology of the lumen.

16. The apparatus as defined in claim 1 wherein the display device comprises an analog recorder.

17. A method of mapping an interior surface of a section of a lumen of a patient's vasculature, the method comprising:

inserting a guide wire percutaneously and transluminally within a lumen of a patient's vasculature;

providing a catheter having a distal end, a portion defining a guide wire lumen, and a plurality of contacts circumferentially disposed on the distal end, each one of the plurality of contacts having a feature that varies as a function of a displacement imposed on the contact by the interior surface, the catheter configured for percutaneous, transluminal insertion in the patient's vasculature;

inserting the catheter transluminally along the guide wire into a selected section of the lumen so that the plurality of contacts are displaced by the interior surface;

measuring the feature for each one of the plurality of contacts;

correlating the measured feature for each of the plurality of contacts to a displacement for each one of the plurality of contacts; and displaying the displacement for each one of the plurality of contacts.

18. The method as defined in claim 17 wherein the step of correlating the measured feature comprises a step of comparing the measured feature to a stored calibration table containing displacements as a function of value of the feature, and interpolating within the table to compute a displacement corresponding to the measured feature.

19. The method as defined in claim 17 wherein the step of displaying the displacement comprises generating and displaying a three-dimensional image of the interior surface of the section.

* * * * *